Figure 1:
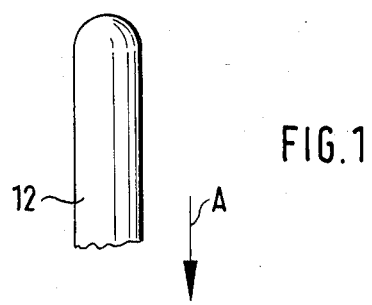

United States Patent [19]

Herold

[11] Patent Number: 4,779,770

[45] Date of Patent: Oct. 25, 1988

[54] METERING DISPENSER

[75] Inventor: Wolf-Dietrich Herold, Seefeld, Fed. Rep. of Germany

[73] Assignee: ESPE Stiftung & Co. Produktion und Vertriebs KG, Seefeld, Fed. Rep. of Germany

[21] Appl. No.: 143,714

[22] Filed: Jan. 14, 1988

[30] Foreign Application Priority Data

Jan. 30, 1987 [DE] Fed. Rep. of Germany ... 8701486[U]

[51] Int. Cl.$^4$ .............................................. B67D 5/42
[52] U.S. Cl. .................................... 222/391; 604/210; 604/224; 74/169
[58] Field of Search ................................ 604/209–210, 604/224; 74/141.5, 156, 169; 222/325–327, 386, 391

[56] References Cited

U.S. PATENT DOCUMENTS

| | | | |
|---|---|---|---|
| 3,221,409 | 12/1965 | Thiel et al. ...................... | 222/391 X |
| 3,517,668 | 6/1970 | Brickson ............................. | 604/209 |
| 3,977,574 | 8/1976 | Thomas ............................... | 222/391 |
| 4,432,474 | 2/1984 | Hutchinson et al. .......... | 222/402.15 |

FOREIGN PATENT DOCUMENTS

0080793 6/1983 European Pat. Off. .
0109913 5/1984 European Pat. Off. .

*Primary Examiner*—Michael S. Huppert
*Attorney, Agent, or Firm*—Foley & Lardner, Schwartz, Jeffery, Schwaab, Mack, Blumenthal & Evans

[57] ABSTRACT

A metering device for dispensing a flowable substance from a container 10, in which a piston 11 with a piston rod 12 having a toothed portion 16 is disposed, includes a socket 17 adapted to be fixed to the container 10, an actuation lever 18 pivotal relative to the socket 17, a return spring 19 biassing the lever 18 to its rest position, an indexing detent 20 for advancing the piston rod 12 upon depression of the lever 18, and a retaining detent 21 for retaining the piston rod 12 in its respective position when the actuation lever 18 is released. The socket 17, actuation lever 18, reset spring 19, indexing detent 20 and retaining detent 21 are formed as one integral part injection-molded from synthetic resin. The socket 17 includes a slide 25 for fixing the part to a flange 14 provided at the rear end of the container 10.

11 Claims, 1 Drawing Sheet

METERING DISPENSER

DESCRIPTION

A prior-art metering device for dispensing a flowable substance is known from EP-A-No. 0,080,793, which comprises a container for receiving the substance, a piston disposed in the container and actuated by a piston rod having a toothed portion and a mechanism for advancing the piston relative to the container. The dvancing mechanism includes an actuation lever, a spring biassing the lever to a rest position, and an indexing detent which is connected to the lever and resiliently engages the toothed portion so that the piston rod and the piston are advanced when the lever is depressed against the biassing force of the spring. Similar dispensers are known from EP-A-No. 0,109,913 and U.S. Pat. No. 3,517,668.

With all these prior-art devices, the container which holds the substance to be dispensed is placed into a two-part receptacle and the two parts are screwed together or joined together by other means. The indexing detent is pivotally mounted on the actuation lever which in turn is pivotally mounted on one part of the receptacle which also holds the piston rod.

Due to this plurality of individual parts, the known construction results in a comparatively heavy, complicated and expensive device. Each time the container with the respective substance is inserted into the device and, when empty, replaced by a new container, the two-part receptacle must be disassembled and thereafter re-mounted. This results in a difficult handling. Further, the large number of individual parts and the fact that the overall device is quite solid and usually made of metal, hinder a sensible handling which is particularly significant for applications in the medical and dental fields.

It is therefore an object of the present invention to provide a metering dispenser which is simple in structure, inexpensive to manufacture, light-weight and easy to handle.

To meet with this object, the metering device for dispensing a flowable substance according to the invention comprises a container for receiving the substance, piston means disposed in the container and having a toothed portion, and means for advancing the piston means relative to the container, the advancing means including socket means adapted to be fixed to a rear end of the container, an actuation lever connected to the socket means, a spring biassing said lever to a rest position, and an indexing detent connected to the lever and resiliently engaging said toothed portion to advance the piston means upon actuation of the lever against the biassing force of said spring, wherein said socket means, said lever, said spring and said indexing detent are formed as one integrally molded part.

The receptacle for the container is thus formed by a socket which engages only the rear part of the container and may be correspondingly small. The fact that this socket together with all functional parts reqprired to advance the piston rod with one hand is formed as one integrally molded part, preferably injection-molded from synthetic resin, results not only in the desired inexpensive manufacture and small overall weight but also in the advantage that the device may be formed as a disposable part that is thrown away with the emptied container. The container and the advancing device may be assembled at the filling site so that a ready-to-operate device is made available to the user.

In a preferred embodiment of the invention, a retaining detent, which in the prior art is formed as a separate catch pivoted to the receptacle and biassed by a separate spring against the toothed portion of the piston rod, is integrally formed on the molded part.

According to a preferred development of the invention, the actuation lever is angularly formed and includes a first arm connected to the socket means and a second arm provided with the return sprng, wherein the piston means extends through a hole formed in the first arm. Due to this shape, a sufficient stroke length for advancing the piston rod upon depression of the actuation lever is achieved in spite of the fact that the indexing detent is integrally formed with the lever.

In a further preferred embodiment, the biassing spring is connected to the free end of the second arm of the actuating lever and extends at an acute angle relative to said arm inwardly towards the outer wall of the container. The spring thus acts on a maximum length of lever arm and may therefore be relatively weak, while still producing the required resetting force even if made of synthetic material. At the same time, a smooth shape of the overall device is achieved.

A particularly advantageous embodiment of the invention provides that the socket means includes a slide for fixing it to a flange at the rear end of the container, the slide being adapted to be brought into engagement with the flange by a sliding movement transverse to the axis of the piston and to the direction of the biassing action of the spring. An efficient and safe connection between the advancing device and the container is thereby achieved in which the actuation of the lever cannot cause a jamming of the piston rod within the socket means even if no close tolerances have been observed in the manufacturing process.

Further advantageous features of the invention relate to achieving a simple shape of the integrally molded part, to obtaining the desired movability of the actuation lever by measures that are easy to verify in manufacture, and to providing the lever with the required stiffness.

Figure 2:
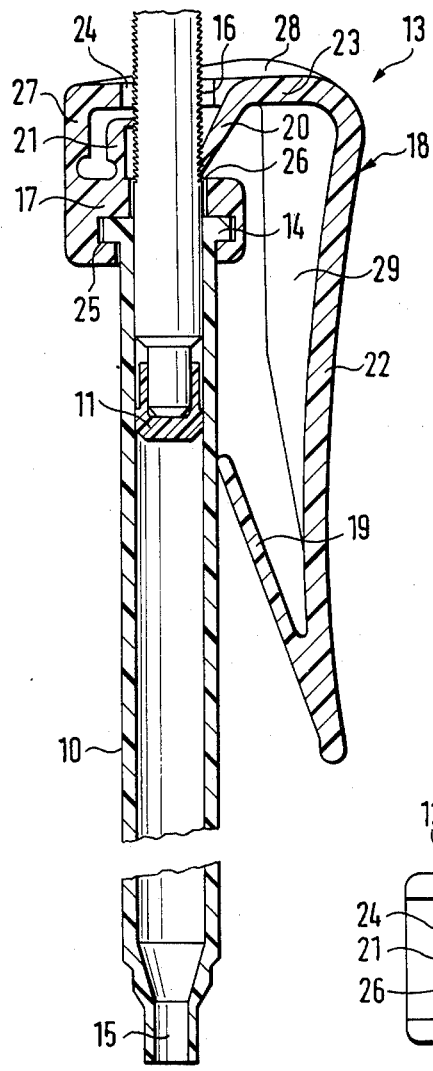

A preferred embodiment of the invention will now be described in detail with reference to the drawing in which FIG. 1 shows a longitudinal section through an assembled device including a container, a piston, a piston rod and a metering fixture, and FIG. 2 is an end view of the metering fixture taken in the direction of the arrow A in FIG. 1.

The device represented in FIG. 1 consists of a cylindrical container 10, a piston 11 slidable in the container 10, a piston rod 12 and an advancing device or metering fixture 13. All these parts are formed as injection-molded synthetic resin parts.

The container 10 has a flange 14 at its rear end. An injection needle, a nozzle tip, or any other dispensing device (not shown) may be fitted or screwed to the front discharge end 15 of the container 10.

The space between the discharge end 15 and the piston 11 serves to receive the substance to be dispensed, which may be, e.g., an etching gel as used in the dental field or any other flowable material. The front end of the piston rod 12 engages the piston 11 and serves to advance the piston for discharging the substance. The piston rod 12 is provided with a toothed main portion 16 which extends over the major length of the piston rod 12 (although only a short length is shown toothed in FIG. 1). The toothing may be formed by a series of individual annular projections, by a thread or the like.

The metering fixture 13, which includes a socket 17, an actuation lever 18, a leaf-type return spring 19, an indexing detent 20 and a retaining detent 21, is formed as an integral part injection-molded from synthetic resin. The lever 18 is angularly formed with one arm 22 extending substantially parallel to the container 10 and the piston rod 12 in the rest position shown in FIG. 1, and the other arm 23 extending perpendicularly thereto and being formed with a hole 24 through which the piston rod 12 passes.

The socket 17 is provided with a slide 25 which is adapted to be slid on the flange 14 of the container 10 in a direction perpendicular to the plane in which the longitudinal section of FIG. 1 has been taken. The socket 17 further includes an opening 26 penetrated by the piston rod 12.

The actuation lever 18 is connected to the socket 17 by means of a connecting leg 27 which is rectangularly joined to the left-hand end of the arm 23 as shown in FIG. 1. At the connection between the leg 27 and the socket 17, the cross-section of the material is reduced so that the lever 18 is easily pivotable with respect to the socket 17. Two ribs 28, which are also seen in FIG. 2, are formed on the outer side of the arm 23. A further rib 29 is formed on the inner side of the arm 22 and extends along the entire length of the arm 22 and the adjacent portion of the arm 23. The ribs 28 and 29 serve to stiffen the angular lever 28.

The indexing detent 20 is integrally formed with the arm 23 of the lever 18 in the vicinity of the hole 24 and extends at an acute angle to the arm 23. The detent 20 is biassed towards the piston rod 12 so that teeth formed at the inner free end of the detent 20 engage the toothed portion 16 of the piston rod 12. A retaining detent 21 is integrally formed with the socket 17 inwardly of the connection between the leg 27 and the socket 17. Again, a reduction in crosc cection serves to increase the movability of the detent 21 relative to the socket 17. At the free end of the retaining detent 21, which is biassed towards the piston rod 17, a number of teeth are provided which engage the toothed portion 16. As appears from FIG. 1, the retaining detent 21 is positioned within the space surrounded by the socket 17, the connecting leg 27 and the arm 23 of the actuation lever 18.

The leaf-type return spring 19 is integraly formed at the free end of the arm 22 of the lever 18 and extends at an acute angle thereto and upwardly according to FIG. 1 with its own free end bearing against the outer wall of the container 10. The spring 19 is thus also positioned inside the lever 18 so that an overall closed shape of the metering fixture 13 is achieved.

To assemble the device shown in FIG. 1, the piston 11 is introduced into the container 10 which has been filled with the substance to be dispensed. Subsequently, the metering fixture 13 is mounted by sliding the slide 25 onto the flange 14 in a direction which extends perpendicular to the plane in which the cross-section of FIG. 1 has been taken. The piston rod 12 is then inserted through the hole 24 in the arm 23 of the lever 18 and through the opening 26 in the socket 17 until it engages the piston 11 as shown in FIG. 1. The toothed portion 16 of the piston rod and the teeth provided on the indexing detent 20 and retaining detent 21 are shaped so as to permit movement of the piston rod 12 in this direction.

In use, the operator depresses the arm 22 of the lever 18 towards the container 10 thereby pivoting the lever 18 in the clockwise sense according to FIG. 1 about the location where the leg 27 is connected to the socket 17. During this pivotal movement, the indexing detent 22 moves downwardly in FIG. 1 and, due to its engagement with the toothed portion 16, pushes the piston rod 12 downwardly. The piston 11 is thereby advanced and the substance is dispensed from the container 10 through the lower discharging end 15. When the lever 18 is released, the return spring 19 will move it back to its rest position by a counter-clockwise pivotal motion according to FIG. 1, while the teeth provided at the free end of the indexing detent 20 slide upwardly over the toothed portion 16 of the piston rod 12. At this time, the retaining detent 21 prevents the piston rod 12 from being retracted. When the actuation lever 18 is again depressed, the piston rod 12 is further advanced upwardly.

When the piston 11 has reached its extreme forward position behind the discharging end 15 and the container 10 has been emptied, the entire device including the piston rod 12 and the metering fixture 13 may be disposed of. This is permissible since all parts of the device are manufactured as low-cost parts molded from plastics.

I claim:

1. A metering device for dispensing a flowable substance, comprising
   (a) a container for receiving said substance,
   (b) piston means disposed in said container and having a toothed portion, and
   (c) means for advancing said piston means relative to said container and including
      (c.1) socket means adapted to be fixed at a rear end of said container,
      (c.2) an actuation lever connected to said socket means,
      (c.3) a spring biassing said lever to a rest position, and
      (c.4) an indexing detent connected to said lever and resiliently engaging said toothed portion to advance said piston means upon actuation of said lever against the biassing force of said spring,
   wherein said socket means, said lever, said spring and said indexing detent are formed as one integrally molded part.

2. The device of claim 1, wherein said advancing means further includes a retaining detent integrally formed with said molded part and resiliently engaging said toothed portion to prevent a reverse motion of said piston means when said lever is released.

3. The device of claim 1, wherein said molded part is formed by injection molding from synthetic resin.

4. The device of claim 2, wherein said lever is angularly formed and includes a first arm connected to said socket means and a second arm provided with said spring, said piston means extending through a hole formed in said first arm.

5. The device of claim 4, wherein said spring is connected to the free end of said second arm, extends at an acute angle relative thereto, and contacts an outer wall of said container.

6. The device of claim 4, wherein said indexing detent is connected to said first arm on the side of said hole opposite to the location where the first arm is connected to said socket means, and etends at an acute angle relative to said first arm.

7. The device of claim 6, wherein said retaining detent is connected to said socket means on the side of said hole opposite to said indexing detent.

8. The device of claim 7, wherein said first arm is connected to said socket means through a connecting portion which extends substantially parallel to said second arm, said retaining detent being disposed between said connecting portion and said second arm.

9. The device of claim 8, wherein the material of said molded part is reduced in cross-section at the location where said connecting portion joins said socket means.

10. The device of claim 4, wherein said lever is formed with stiffening ribs provided at the outer side of said first arm and at the inner side of said second arm.

11. The device of claim 1, wherein said socket means has an opening penetrated by said piston means and a slide for fixing said socket means at a flange provided a rear end of said container, said slide being adapted to be brought into engagement with said flange by a sliding movement transverse of the axis of said piston means and to the direction of the biassing action of said spring.

* * * * *